United States Patent [19]

Ueberschaer

[11] 4,406,171

[45] Sep. 27, 1983

[54] LIQUID SAMPLING DEVICE

[75] Inventor: Hubert J. Ueberschaer, Hartsdale, N.Y.

[73] Assignee: Mobil Oil Corporation, New York, N.Y.

[21] Appl. No.: 286,481

[22] Filed: Jul. 24, 1981

Related U.S. Application Data

[63] Continuation of Ser. No. 68,995, Aug. 23, 1979, abandoned.

[51] Int. Cl.³ .............................................. G01N 1/10
[52] U.S. Cl. .............................. 73/864.62; 73/864.51
[58] Field of Search ........... 73/864.62, 864.61, 864.51, 73/864.23, 864.63; 33/126.4; 417/546

[56] References Cited

U.S. PATENT DOCUMENTS

| | | | |
|---|---|---|---|
| 378,338 | 2/1888 | Shelnutt | 417/546 |
| 587,455 | 8/1897 | Sawyer | 417/546 |
| 1,621,857 | 3/1927 | Seraphin | 73/864.61 |
| 1,963,080 | 6/1934 | Featherstone | 73/864.62 X |
| 2,059,999 | 11/1936 | Rainville, Sr. | 73/864.62 |
| 2,274,869 | 3/1942 | Pfeiffer | 73/864.62 |
| 3,273,394 | 9/1966 | Chaney | 73/864.61 |
| 3,692,490 | 9/1972 | Hall | 73/864.62 |
| 3,950,999 | 4/1976 | Edwards | 73/864.61 |
| 4,196,627 | 4/1980 | Locher | 33/126.4 R X |

*Primary Examiner*—Daniel M. Yasich
*Attorney, Agent, or Firm*—C. A. Huggett; M. G. Gilman; J. F. Powers, Jr.

[57] ABSTRACT

A liquid sampling device comprises a cylinder with a piston and a liquid outlet at its top. Liquid inlet ports are disposed at the bottom of the cylinder with one-way entry valves to admit the liquid which is to be sampled into the cylinder. The piston has by-pass ports controlled by one-way valves which permit the sampled liquid to pass upwards through the piston.

The device is operated by lowering it into the liquid to be sampled by means of a line attached to a piston rod connected to the piston. The liquid is then drawn into the cylinder by means of the piston and the liquid sample removed.

8 Claims, 3 Drawing Figures of the liquid 9, such as a cargo tank of an oil tanker.

LIQUID SAMPLING DEVICE

This is a continuation of application Ser. No. 068,995 filed Aug. 23, 1979, now abandoned.

CROSS REFERENCE TO RELATED APPLICATIONS

U.S. patent application Ser. No. 937,293 filed Aug. 28, 1978 by J. Hartley Locher, now U.S. Pat. No. 4,196,627, describes a liquid sampling device of a different type.

BACKGROUND OF THE INVENTION

The present invention relates to a device for obtaining a sample of liquid from the bottom of a liquid-filled container. More particularly, the invention relates to a device for obtaining a sample of water or water-oil emulsion from underneath the crude oil in the cargo tank of an oil tanker.

In many instances, cargo oil, e.g. crude or refined oil which is loaded onto tankers is contaminated with substantial amounts of water. If payment for the oil is based on the measured volume of total liquid in the cargo tanks, the final cost to a buyer may be higher than it should be because he pays for the useless water at cargo oil prices. In many actual cargo oil purchasing situations, the buyer is allowed to deduct the volume of water in the cargo tanks only if he can prove that it was pumped aboard with the cargo oil and was not already present in the tanks before the cargo oil was loaded.

Since water inadvertently left in the tanks (e.g. seawater used for ballast, etc.), will have a substantially different composition from the water loaded with the cargo oil (e.g. formation water produced with the crude or condensate from steam used in processing the produced oil,), the origin of the water in question can readily be established if a sample of the water can be obtained from a cargo tank for analysis after it has been loaded.

Further, by knowing the origin of any water in a loaded cargo tank, steps can be taken to alleviate the contamination problem. That is, if the water is being pumped in with the cargo oil, further processing of the cargo oil can be undertaken to remove the water before loading or if the water is originally present in the tank, further steps can be taken aboard the ship to remove such water before loading.

SUMMARY OF THE INVENTION

The present invention provides a simple, self-contained apparatus for obtaining a sample of liquid from near the bottom of a liquid-filled container such as the cargo tank aboard an oil tanker. According to the present invention the sampling device comprises a cylinder with an internal piston which can be operated by means of a piston rod extending through the top cover on the cylinder. The bottom cover of the cylinder has liquid inlet ports which communicate with the interior of the cylinder; these inlets are provided with one-way valves which permit liquid to enter the cylinder but not to leave it. The piston is fitted with by-pass ports fitted with one way valves; these valves permit liquid to flow upwards through the by-pass ports but not in the reverse direction. The cylinder has a liquid outlet adjacent the top cover. It is also fitted with means such as legs which are capable of supporting the device at a desired height above the bottom of the container.

When a liquid sample is to be obtained, the sampling device is lowered down through the liquid in the container by means of a line, e.g. a cord or a chain attached to the top of the piston rod. During this part of the operation, the piston will be at the top of its travel, i.e. adjacent the top cover of the cylinder. When the device reaches the bottom of the container, the legs or other supporting means begin to take the weight of the cylinder off the line. This permits the piston to descend into the cylinder and as it does so, any liquid in the cylinder below the piston passes upwards through the by-pass ports in the piston to the portion of the cylinder above the piston. When sufficient time has elapsed for the piston to descend fully in the cylinder, the device is drawn up by means of the line attached to the piston rod. Initially, the piston rises in the cylinder as the line is drawn up. As it does so, the liquid surrounding the bottom of the device is drawn through the inlet ports into the portion of the cylinder below the piston; at the same time, the liquid in the cylinder above the piston is expelled through the liquid outlet. Eventually, the piston reaches the top of its travel and the cylinder beneath the piston is filled with the liquid to be sampled. As the device is drawn up by means of the line, escape of the sampled liquid is prevented by the one-way valves on the inlet ports. Finally, when the sampled liquid is to be collected, the piston is depressed to transfer the sampled liquid through the by-pass ports to the region above the piston; the piston is then raised so as to expel the sampled liquid through the outlet port from which it may be collected in a suitable container.

Before the device is lowered down through the liquid in the container it may, if desired, be filled with clean oil. This can be done by placing the lower part of the device in a bucket of the clean oil and raising the piston so as to draw the oil into the cylinder. The device is then lowered into the container by means of the line, as described above. This initial filling step may be desirable if the oil in the container is dirty or viscous in nature; the clean oil prevents passage of dirt through the valves in the sampler and can also be more easily displaced through the by-pass ports and expelled from the outlet than the more viscous cargo oil. Suitable types of lighter oil for this step are lubricating oil, diesel oil and fuel oil.

DESCRIPTION OF PREFERRED EMBODIMENTS

Figure 1:
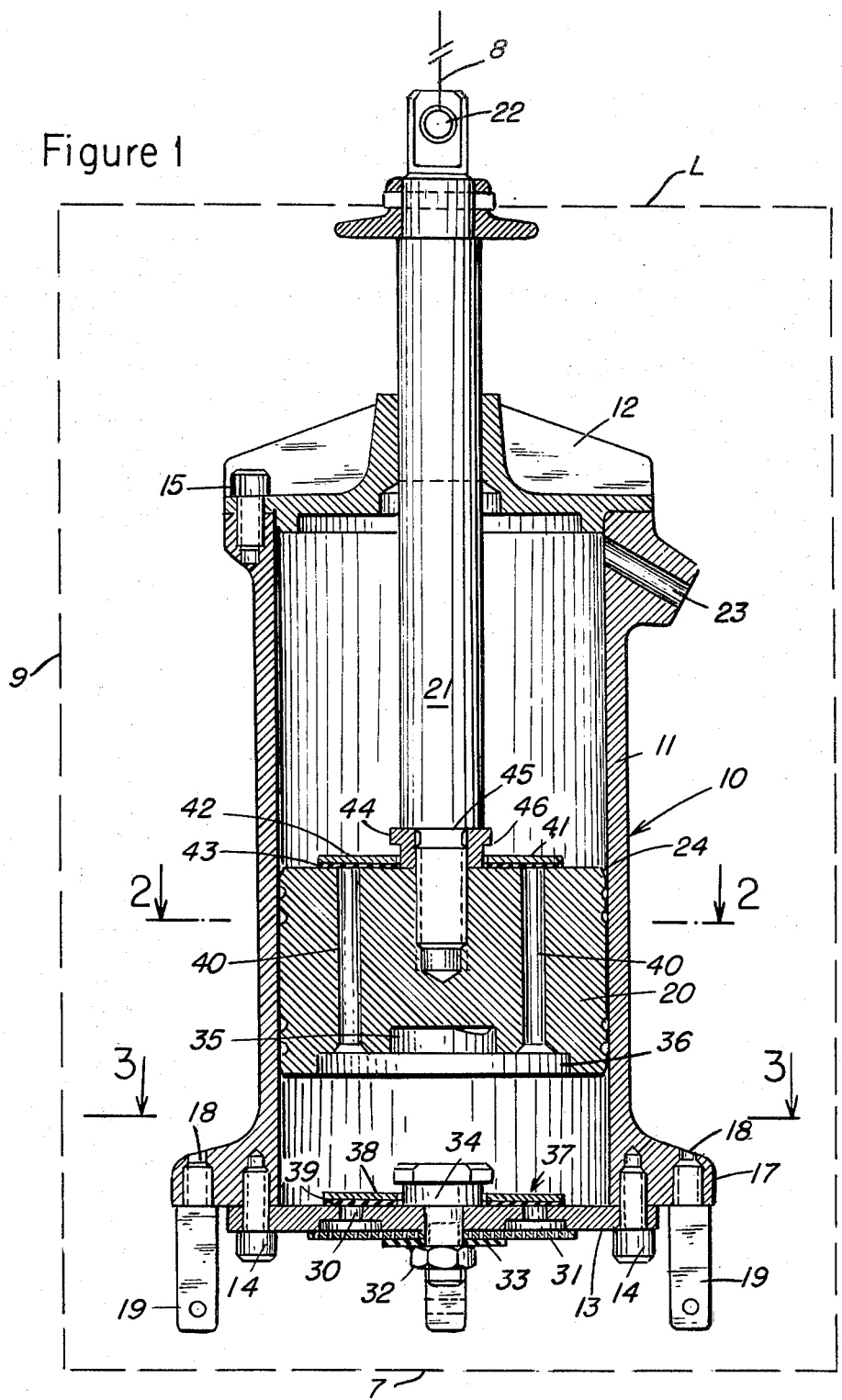
FIG. 1 is an elevation in section of one form of the sampling device.
Figure 2:
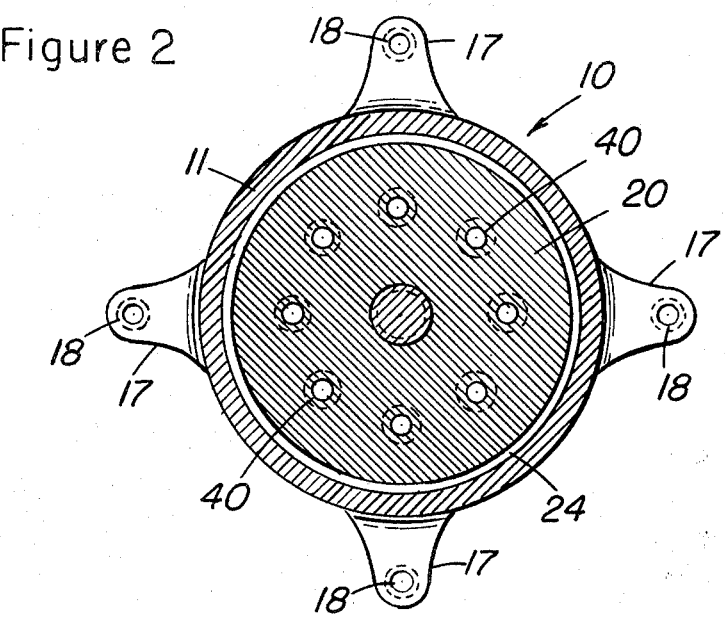
FIG. 2 is a cross-section along line 2—2' of FIG. 1.
Figure 3:
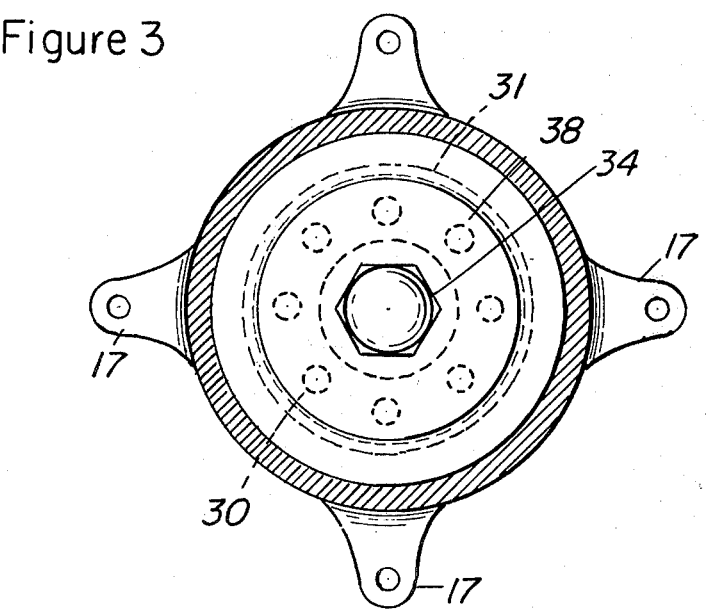
FIG. 3 is a cross-section along line 3—3' of FIG. 1.

The device 10 comprises a cylindrical barrel 11 fitted with a top cover 12 and a bottom cover 13. The covers are held together by means of the bottom screws 14 and top screws 15. The cylinder barrel 11 and the top and bottom covers 12 and 13 are suitably made of brass while screws 14 and 15 are suitably of bronze or stainless steel in order to avoid corrosion from alternate contact with oil and salt water. Barrel 11 has a bottom flange 17 which has a number (4) of axial screw holes 18 around its periphery. Legs 19 are screwed into the screw holes 18 in the flange in order to regulate the height at which the device stands above the bottom of the liquid 9, such as a cargo tank of an oil tanker.

A heavy brass piston 20 fits closely within cylinder barrel 11 so as to provide a sliding but substantially liquid-tight fit with the barrel. A piston rod 21, suitably of bronze, is screwed into the piston and extends through an aperture in top cover 12. An eye 22 for the lowering and raising line 8 is provided on the end of piston rod 21.

A liquid outlet spigot 23 is provided in the side of barrel 11 near top cover 12. In order to ensure that piston 20 can be drawn to the top of its stroke without trapping liquid above the top of the passageway in spigot 23, a relief 24 may be provided on the outer periphery of the upper surface of the piston.

The lower cover 13 has eight inlet ports 30 evenly spaced radially around its central axis. These ports are covered on the outside of cover 13 by a strainer 31 which is secured by a nut 32 and washer 33 on screwed boss 34 which extends through cover 13. Piston 20 has a central recess 35 in its lower surface to accommodate boss 34 when the piston is at the bottom of its stroke. Recess 35 has a more shallow radial extension 36 to accommodate inlet valve 37 which fits against the inner surface of bottom cover 13 to cover inlet ports 30. Valve 37 comprises a composite annular plate comprising a bronze disc 38 and neoprene disc 39 with the neoprene disc face downwards so as to provide a liquid-tight seal against bottom cover 13 when pressure is exerted on the top face of the valve plate from above. The plate is a freely sliding fit on the upper portion of boss 34 so that when valve 37 slides upwards on boss 34, liquid flow in an upward direction may take place through inlet ports 30.

Piston 20 has a number of axial by-pass ports 40 evenly spaced radially around its central axis. These ports provide liquid flow communication between the portion of the cylinder beneath the piston and the portion above the piston. These by-pass ports open onto the upper surface of piston 20 where there is a one-way plate valve 41 similar in construction to valve 37. Valve 41 is of composite construction, comprising an annular bronze upper disc 42 and a lower neoprene disc 43 which seals against the upper surface of piston 20 when liquid pressure is exerted on valve 41 from above. Valve 41 is a freely sliding fit on annular boss 44 which is secured to the upper face of piston 20 by means of a shoulder 45 on piston rod 21.

In use, the device is first filled with clean oil such as lubricating oil or fuel oil. This is done by lowering piston 20 in the cylinder 11 to the bottom of its stroke. The lower part of the device is then immersed in the clean oil which may be in a suitable container such as a bucket. Piston rod 21 is then withdrawn manually so as to raise piston 20 in cylinder 11. This draws the light oil into cylinder 11 through strainer 31 and inlet ports 30. One-way valve 37 acts to permit the flow of liquid in this direction by sliding axially up boss 34. When piston 20 is at the top of its stroke adjacent top cover 12 the cylinder will be full of the clean oil and the device may be removed from the bucket or other container. Escape of the oil from the cylinder is prevented by the action of valve 37: the liquid pressure on the top of the valve plate seals the valve firmly over the inlet ports 30 thereby retaining the oil within the cylinder.

The device is then lowered into the liquid L filled container 9 from which the sample is to be taken. The lowering is carried out by means of a line 8 such as a steel wire or chain attached to eye 22 in piston rod 21, so as to retain piston 20 at the top of its stroke in the cylinder. The lowering is continued until the legs 19 on the bottom of the device rest on the bottom 8 of the liquid filled container. The tension on the line is then released so that piston 20 slides down cylinder barrel 11 under its own weight to which end, piston 20 is of relatively massive construction so as to be able to overcome the frictional and viscous forces which it encounters at this point. As piston 20 slides down cylinder 11 the light oil retained below the piston passes through by-pass ports 40 into the portion of the cylinder above the piston; the action of one-way valve 41 permits this flow to take place by sliding axially up boss 44 as far as permitted by retaining shoulder 46.

The liquid near the bottom 7 of the container 9 is then sampled by restoring tension on the line attached to piston rod 21 so as to draw piston 20 up cylinder barrel 11 until it reaches the top of its stroke, adjacent top cover 12. As the piston rises in the cylinder the light oil which was above the piston is expelled through spigot 23. At the same time, the liquid to be sampled is drawn into the cylinder through strainer 31 and inlet ports 30, as permitted by valve 37. When the piston reaches the top of its stroke the cylinder will be filled with the liquid to be sampled; further tension on the line will then draw the device up through the liquid-filled container 9 to the place where the sample is to be collected. The sampled liquid is retained in the portion of the cylinder beneath the piston by means of one-way valve 37.

Finally, the sampled liquid is collected. To do this, the sampling device containing the sampled liquid is set down, e.g. on the deck of the tanker and piston 20 is lowered in the cylinder 11 under its own weight or by a downward force applied manually on piston rod 21. This action transfers the sampled liquid to the portion of the cylinder above the piston through by-pass ports 40 as permitted by the action of one-way valve 41. The sampled liquid may then be expelled from the device by raising piston 20 in cylinder 11; this may be done by pulling piston rod 21 upwards manually. The action of one-way valve 41 prevents the sampled liquid escaping through by-pass ports 40. The liquid expelled through spigot 23 may be collected in a suitable container, such as a collection bottle, for analysis.

The height above the bottom of the container 9 at which the sample is taken may be varied by the use of legs 19 of different lengths. A set of legs of varying lengths may be supplied with each device so as to facilitate change of sampling depth. Other devices for achieving the same purpose may also be used, for example, an axially-slotted skirt secured to the bottom cover 13 by means of radial screws passing through the slots. Loosening the screws would permit the skirt to be moved axially with respect to the rest of the device and the position chosen would be retained when the screws were tightened again. The skirt would be provided with suitable apertures to permit the liquid to be sampled to obtain access to the inlet ports in the bottom cover. The axial slots could, if desired, be replaced by helical slots which would permit the sampling depth to be altered by a rotary movement of the skirt.

Rapid sinking of the device is ensured by its relatively massive construction. The mass of the device also helps to maintain it upright on the bottom 7 of the container 9 when the liquid to be sampled is drawn in by withdrawal of the piston. A relatively good sliding—but fluid tight—fit between the piston and the barrel is also helpful in this respect.

The plate valves described above may, if desired, be replaced by other suitable one-way valves, e.g. reed valves, flapper valves or ball check valves. The valves may, of course, be made of materials other than those specifically described; for example, ball valves may be made of steel balls with neoprene or polytetrafluoroethylene seals or the plate valves shown may be made entirely of plastic resins. Other variations will be apparent to those skilled in the art.

I claim:

1. A liquid sampling device which comprises:
   (i) a cylinder having a top end and a bottom end, and a liquid outlet adjacent the top end,
   (ii) a massive weighted piston slidably disposed within the cylinder and normally at rest at said bottom end of the cylinder,
   (iii) a piston rod fixed to the piston and extending beyond the top end of the cylinder,
   (iv) at least one inlet port for the liquid to be sampled at the bottom end of the cylinder,
   (v) first valve means comprising a first plate which is vertically movable from a lower sealing position covering the inlet port and an upper flow position which permits liquid flow into the cylinder through the inlet port,
   (vi) at least one liquid by-pass port in the piston, and
   (vii) second valve means comprising a second plate which is vertically movable from a lower sealing position covering the by-pass port to an upper flow position which permits liquid flow through the by-pass port in an upward direction.

2. A sampling device according to claim 1 which includes means for supporting the device in an upright position at a predetermined height above the bottom of a container containing the liquid to be sampled.

3. A sampling device according to claim 1 which includes a strainer positioned underneath the inlet port to strain liquid entering the cylinder through the inlet port.

4. A sampling device according to claim 1 in which the first plate valve comprises a vertically movable disc having a resilient sealing surface.

5. A sampling device according to claim 1 in which the second plate valve comprises a vertically movable disc having a resilient sealing surface.

6. A method of sampling a liquid within a container employing a sampling device having a cylinder having a piston of massive weight construction having at least one by-pass port and first one way valve means, said piston being slidably disposed within the cylinder, a piston rod attached to the piston and extending beyond the top end of the cylinder, and a liquid outlet at the top end of the cylinder, which method comprises:
   (i) initially withdrawing the piston rod whereby the piston is brought to the top of its stroke in the cylinder to draw a liquid into the cylinder, which liquid is then expelled from the cylinder in step (iv),
   (ii) lowering the sampling device down through a container of liquid by means of a line attached to the piston rod attached to the piston, whereby the piston is retained at the top of its stroke within the cylinder until the device reaches the desired sampling height in the container,
   (iii) causing the piston to descend within the cylinder to the bottom of its stroke,
   (iv) withdrawing the piston rod by means of the line whereby the piston is brought to the top of its stroke in the cylinder and the liquid to be sampled is drawn into the cylinder beneath the piston through second one way valve means at the lower end of said cylinder,
   (v) causing the piston to descend in the cylinder to the bottom of its stroke whereby the liquid drawn into the cylinder is transferred to the portion of the cylinder above the piston, and
   (vi) withdrawing the piston rod whereby the piston is brought to the top of its stroke in the cylinder and the liquid in the cylinder is expelled from the liquid outlet.

7. A method according to claim 6 in which the liquid to be sampled comprises water underlying oil within the cargo tank of an oil tanker.

8. A method of sampling a liquid within a container employing a sampling device having a cylinder having a piston of massive weight construction having at least one by-pass port and first one way valve means, said piston being slidably disposed within the cylinder, a piston rod attached to the piston and extending beyond the top end of the cylinder, and a liquid outlet at the top end of the cylinder, which method comprises:
   (i) lowering the sampling device down through a container of liquid by means of a line attached to the piston rod attached to the piston, whereby the piston is retained at the top of its stroke within the cylinder until the device reaches the desired sampling height in the container,
   (ii) causing the piston to descend within the cylinder to the bottom of its stroke,
   (iii) withdrawing the piston rod by means of the line whereby the piston is brought to the top of its stroke in the cylinder and the liquid to be sampled is drawn into the cylinder beneath the piston through second one way valve means at the lower end of said cylinder,
   (iv) causing the piston to descend in the cylinder to the bottom of its stroke whereby the liquid drawn into the cylinder is transferred to the portion of the cylinder above the piston, and
   (v) withdrawing the piston rod whereby the piston is brought to the top of its stroke in the cylinder and the liquid in the cylinder is expelled from the liquid outlet.

* * * * *